(12) United States Patent
Morita et al.

(10) Patent No.: US 8,748,142 B2
(45) Date of Patent: Jun. 10, 2014

(54) CULTURE OF CARDIOVASCULAR CELLS ON A MATRIX AND METHOD FOR REGENERATING CARDIOVASCULAR TISSUE

(75) Inventors: Shinichiro Morita, Kyoto (JP); Toshiharu Shin'Oka, Tokyo (JP); Yasuharu Imai, Tokyo (JP)

(73) Assignees: Gunze Limited, Kyoto (JP); Tokyo Women's Medical University, Tokyo (JP)

( * ) Notice: Subject to any disclaimer, the term of this patent is extended or adjusted under 35 U.S.C. 154(b) by 275 days.

(21) Appl. No.: 12/616,000

(22) Filed: Nov. 10, 2009

(65) Prior Publication Data

US 2010/0055791 A1 Mar. 4, 2010

Related U.S. Application Data

(63) Continuation of application No. 10/070,938, filed as application No. PCT/JP00/06129 on Sep. 8, 2000, now abandoned.

(30) Foreign Application Priority Data

Sep. 9, 1999 (JP) ................. 1999-255803

(51) Int. Cl.
*C12N 11/08* (2006.01)
*C12N 5/07* (2010.01)
*A61F 2/02* (2006.01)
*A61F 2/06* (2013.01)
*A61F 2/24* (2006.01)
*A61L 27/38* (2006.01)
*A61L 27/56* (2006.01)
*A61L 27/48* (2006.01)
*C12N 5/00* (2006.01)
*A61L 27/58* (2006.01)
*C12N 5/071* (2010.01)

(52) U.S. Cl.
CPC ......... *A61L 27/3886* (2013.01); *A61L 27/3843* (2013.01); *A61L 27/3839* (2013.01); *A61L 27/383* (2013.01); *A61L 27/56* (2013.01); *C12N 2502/1323* (2013.01); *A61L 2430/20* (2013.01); *A61L 27/48* (2013.01); *A61L 27/3826* (2013.01); *C12N 5/0068* (2013.01); *A61L 27/3808* (2013.01); *A61L 27/3804* (2013.01); *A61L 27/58* (2013.01); *C12N 5/069* (2013.01); *C12N 2533/40* (2013.01)
USPC ............ 435/180; 435/395; 435/396; 424/423

(58) Field of Classification Search
CPC ........ C12N 11/08; C12N 5/06; C12N 5/0661; C12N 5/0691; C12N 5/0697; A61F 2/02; A61F 2/06; A61F 2/24
See application file for complete search history.

(56) References Cited

U.S. PATENT DOCUMENTS

| | | | |
|---|---|---|---|
| 4,546,500 | A | 10/1985 | Bell |
| 4,725,273 | A | 2/1988 | Kira |
| 5,509,930 | A | 4/1996 | Love |
| 5,855,610 | A | 1/1999 | Vacanti et al. |
| 5,863,531 | A | 1/1999 | Naughton et al. |
| 5,882,929 | A | 3/1999 | Fofonoff et al. |
| 6,534,084 | B1 | 3/2003 | Vyakarnam et al. |
| 6,719,789 | B2 | 4/2004 | Cox |

FOREIGN PATENT DOCUMENTS

| | | |
|---|---|---|
| EP | 0 277 678 | 8/1988 |
| EP | 0 734 736 | 10/1996 |
| EP | 0 274 898 | 7/1998 |
| JP | 62-44260 | 2/1987 |
| JP | 63-255068 | 10/1988 |
| JP | 63-272355 | 11/1988 |
| JP | 1-230366 | 9/1989 |
| JP | 2-167156 | 6/1990 |
| JP | 323864 | 1/1991 |
| JP | 5-76588 A | 3/1993 |
| JP | 5-269196 A | 10/1993 |
| JP | 6-292716 | 10/1994 |
| JP | 10-234844 A | 9/1998 |
| WO | WO 84/00302 | 2/1984 |
| WO | WO 96/08213 | 3/1996 |
| WO | WO 96/38188 | 12/1996 |
| WO | WO 96/40175 | 12/1996 |

OTHER PUBLICATIONS

European Search Report dated Jan. 26, 2006 for application No. EP 00957031.
Shinoka, T. et al. 1998 "Creation of Viable Pulmonary Artery Autografts through Tissue Engineering" *The Journal of Thoracic and Cardiovascular Surgery* 115(3):536-545.

*Primary Examiner* — David M Naff
(74) *Attorney, Agent, or Firm* — Knobbe, Martens, Olson & Bear, LLP

(57) ABSTRACT

Materials for culturing cardiovascular tissues wherein a sponge made of a bioabsorbable material is reinforced with a reinforcement made of a bioabsorbable material.

10 Claims, 2 Drawing Sheets

CULTURE OF CARDIOVASCULAR CELLS ON A MATRIX AND METHOD FOR REGENERATING CARDIOVASCULAR TISSUE

RELATED APPLICATIONS

This application is a continuation of application Ser. No. 10/070,938, filed Jun. 4, 2002 now abandoned, which is U.S. National Phase under 35 U.S.C. §371 of International Application PCT/JP00/06129, filed Sep. 8, 2000 designating the U.S., and published in English as WO 01/17572 on Mar. 15, 2001, which claims priority to Japanese Patent Application No. 1999-255803, filed Sep. 9, 1999.

BACKGROUND OF THE INVENTION

1. Field of the Invention

The present invention relates to a matrix for culturing cardiovascular cells to regenerate cardiovascular tissue and a method for regenerating cardiovascular tissue such as an artificial blood vessel, cardiac valve, pericardium, etc.

2. Description of the Related Art

In the field of artificial vessels, for instance, those made of non-bioabsorbable polymers are widely used. An artificial vessel (GORE-TEX), for example, is used most frequently in a clinical field. Such non-bioabsorbable artificial vessel is excellent in physical properties; however, because of the non-bioabsorbability, it remains in vivo as a foreign body for a long period of time after implantation. Further, when the non-bioabsorbable artificial vessel is implanted into the body of a child, another surgery for replacement is necessary since the non-bioabsorbable artificial vessel does not expand with the growth of the autogeneous blood vessel.

A tissue regeneration method employing tissue engineering techniques has recently been developed, wherein cells of autogeneous tissue are seeded and cultured on a scaffold made of a bioabsorbable polymer so as to regenerate the autogeneous tissue. There have been published quite a few research reports of the tissue regeneration method applied to skin regeneration (M. L. Cooper, L. F. Hansbrough, R. L. Spielvogel, et al.: In vivo optimization of a living dermal substitute employing cultured human fibroblasts on a biodegradable polyglycolic acid or polyglactin mesh. Biomaterials, 12:243-248, 1991) and cartilage regeneration (C. A. Vacanti, R. Langer, et al.: Synthetic polymers seeded with chondrocytes provide a template for new cartilage formation. Plast. Reconstr. Surg., 88:753-759, 1991).

If a blood vessel can be regenerated in the same manner as described above, growth of the regenerated blood vessel is expected since it is regenerated by using autogeneous tissue and no longer necessitates the use of anti-coagulants.

SUMMARY OF THE INVENTION

An object of the present invention is to provide a matrix which allows cells to sufficiently adhere thereto, provides an optimum scaffold for cell proliferation, maintains satisfactory blood flow resistance in vivo till autogeneous tissue is regenerated, and is ultimately decomposed and absorbed in vivo.

The present invention provides a matrix for culturing cardiovascular tissue and a method for regenerating cardiovascular tissue of the following items.

Item 1. A matrix for culturing cardiovascular cells to regenerate cardiovascular tissue comprising a sponge made of a bioabsorbable material and a reinforcement made of a bioabsorbable material.

Item 2. The matrix for culturing cardiovascular cells to regenerate cardiovascular tissue according to item 1, wherein the bioabsorbable material is at least one member selected from the group consisting of polyglycolic acid, polylactic acid (D form, L form, DL form), polycaprolactone, glycolic acid-lactic acid (D form, L form, DL form) copolymer, glycolic acid-caprolactone copolymer, lactic acid (D form, L form, DL form) caprolactone copolymer, poly (p-dioxanone) and the like.

Item 3. The matrix for culturing cardiovascular cells to regenerate cardiovascular tissue according to item 1 for use in regenerating an artery, wherein the sponge comprises a lactic acid-caprolactone copolymer and the reinforcement comprises polylactic acid.

Item 4. The matrix for culturing cardiovascular cells to regenerate cardiovascular tissue according to item 1 for use in regenerating a vein, wherein the sponge comprises a lactic acid-caprolactone copolymer and the reinforcement comprises polyglycolic acid.

Item 5. The matrix for culturing cardiovascular cells to regenerate cardiovascular tissue according to item 1 for use in regenerating a cardiac valve or a pericardium, wherein the sponge comprises a lactic acid caprolactone copolymer and the reinforcement comprises polylactic acid.

Item 6. The matrix for culturing cardiovascular cells to regenerate cardiovascular tissue according to item 1, wherein the sponge has a pore diameter of about 5 μm to about 100 μm.

Item 7. A method for regenerating cardiovascular tissue comprising seeding cells on the matrix of item 1 and culturing the cells.

Item 8. The method for regenerating cardiovascular tissue according to item 7, wherein the cardiovascular tissue to be regenerated is a blood vessel.

Item 9. The method for regenerating cardiovascular tissue according to item 7, wherein the cardiovascular tissue to be regenerated is a cardiac valve.

Item 10. The method for regenerating cardiovascular tissue according to item 7, wherein the cardiovascular tissue to be regenerated is a pericardium.

Item 11. The method for regenerating cardiovascular tissue according to item 7, wherein the cells to be seeded are a mixed cell culture of two or three different kinds selected from the group consisting of endothelial cells, smooth muscle cells and fibroblasts.

DETAILED DESCRIPTION OF THE PREFERRED EMBODIMENT

Figure 1:
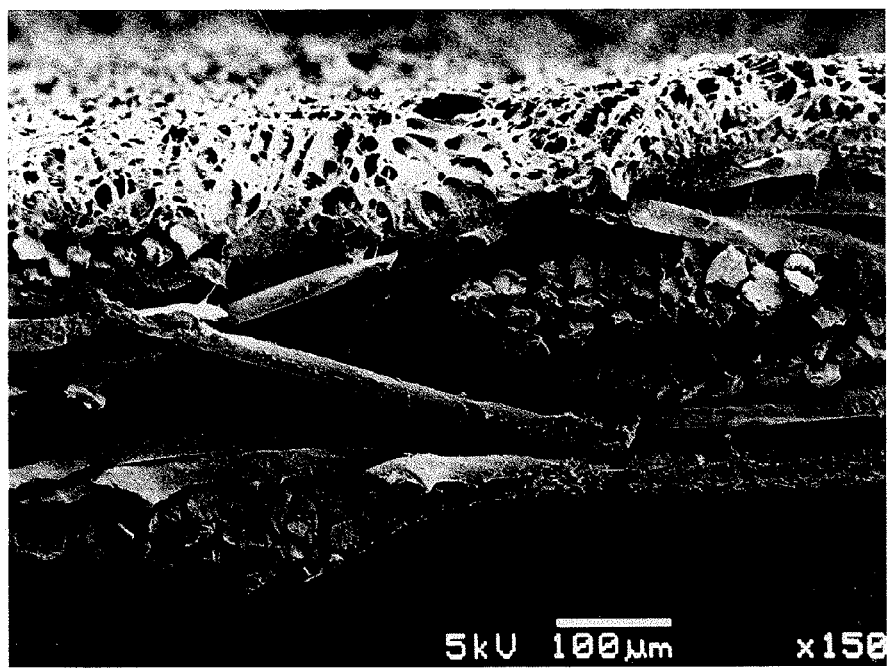
FIG. 1 is a photograph showing a cross-sectional view of a vascular regeneration matrix according to the present invention.

Basic requirements for the matrix for culturing cardiovascular cells to regenerate cardiovascular tissue are an ability to allow cells seeded thereon to adhere firmly thereon and a bioabsorbability which enables the matrix to be absorbed in vivo when a blood vessel is regenerated. A sponge is considered to be the optimum material to fulfill the above requirements.

In the case of using the matrix for regenerating a blood vessel, the matrix is required to maintain an enough strength to endure a blood flow for a certain period of time after implantation till the blood vessel is regenerated in vivo.

The inventors found that the above object is achieved by strengthening, with a reinforcement made of a bioabsorbable material, a sponge made of a bioabsorbable material which is an optimum scaffold for cell proliferation and excellent in cell adhesiveness.

According to the invention, it is preferable that regeneration of cardiovascular tissue be conducted by seeding cells to a matrix for culturing cardiovascular cells and embedding the matrix in vivo to regenerate cardiovascular tissue in vivo.

Examples of bioabsorbable material include polyglycolic acid, polylactic acid (D form, L form, DL form) copolymer, glycolic acid-caprolactone copolymer, lactic acid (D form, L form, DL form)-caprolactone copolymer, poly(p-dioxanone) and the like.

Examples of cardiovascular tissue include blood vessels, cardiac valves, the pericardium and the like.

The matrix of the invention is obtained by strengthening a sponge made of a bioabsorbable material with a reinforcement (in the form of a fiber, nonwoven fabric or film) made of a bioabsorbable materials to be used for the sponge and the reinforcement. In the case of preparing the matrix for regenerating a blood vessel, a sponge made of a lactic acid-caprolactone copolymer may be combined with a reinforcement made of polylactic acid when the blood vessel is an artery, and the same sponge may be combined with a reinforcement made of polyglycolic acid when the blood vessel is a vein. Further, in the case of regenerating a cardiac valve or the pericardium, a sponge made of a lactic acid-caprolactone copolymer may be combined with a reinforcement made of polylactic acid.

The sponge has pores each having such a pore size that cells can suitably be adhered thereto to proliferate and that no blood leakage is caused when the matrix comprising the sponge is implanted as cardiovascular tissue. The pore size may typically be about 1 mm or less, preferably about 5-100 μm. The shape of the matrix may be cylindrical when the cardiovascular tissue to be regenerated is a blood vessel or may be plane when the cardiovascular tissue to be regenerated is a cardiac valve or the pericardium. In the case of regenerating a blood vessel, the length and inside diameter of the matrix may be adjusted depending on the target blood vessel. The thickness of the matrix is chosen depending on the desired period for bio-absorption or ease of suturing. The thickness may typically be about 5 mm or less, preferably from about 500 μm to about 2 mm.

For preparation of the sponge, the following alternative processes, among others, are available.

(1) Lyophilization Process

A substrate polymer solution is poured in a mold, frozen, and, then lyophilized. According to the freezing temperature and polymer concentration, sponges having various pore diameters are obtained (described in Examples).

(2) Elution Process

A water-soluble material is mixed with the substrate polymer solution and, after drying, the water soluble material is washed out with rinse water. The resultant sponge has a pore diameter corresponding to the particle size of the water-soluble material used. In the present case, sucrose can be used with advantage.

The reinforcement must have a greater strength than the sponge. The reinforcement can be selected from among a fiber, nonwoven cloth, film and so on.

The reinforcement is preferably integrated with the sponge and can be located either on the interior surface, inside, or exterior surface of the sponge. However, since the interior surface of the sponge is involved in the adhesion of vascular endothelial cells, it is preferably situated inside or on the exterior surface, although the interior surface may be optionally used.

As to the cells to be seeded, substantially the same kinds of cells are used for various cardiovascular tissues in common. Thus, they are endothelial cells, smooth muscle cells and fibroblasts, and a mixed cell culture of two or three different kinds of cells can be mentioned by way of example. Tissue construction is carried out using such mixed culture cells.

The cultural conditions for the cells to be used and the seeding method are described below.

A. Cell Isolation, Culture, and Propagation

The vascular tissue isolated in a sterile environment is immersed in a cell culture medium and washed with phosphate-buffered saline in a clean bench. Then, on a Petri dish, the tissue is cut into pieces using a surgical knife according to the simple explant technique. Tissue pieces sized about 1-2 mm$^2$ are distributed uniformly on the dish and after about 20 minutes, when the tissue pieces have intimately adhered to the bottom of the dish, a culture medium is added. As the culture medium, Dulbecco's Modified Eagles Medium (DMEM) supplemented with 10% fetal calf serum and 1% antibiotics solution (L glutamine 29.2 mg/ml, penicillin G 1000 U/ml, streptomycin sulfate 10,000 μg/ml) is used. The mixed cells of endothelial cells and fibroblasts begin to migrate from the tissue pieces on the dish after 5-7 days, forming mixed-cell colonies around the explants in a further one week. After another 2-3 weeks, the mixed cells become confluent on the dish. Immediately, a passage is made using 0.25% trypsin and the culture in a 75 cm$^2$ culture flask is started. Generally when the growth in this flask has become confluent, about $2\times10^6$ cells are available. Cell culture is performed under an atmosphere comprising 5% $CO_2$ and 21% $O_2$ and continued until $10\times10^6$ cells have been obtained. While the culture medium is renewed every 4-5 days, the resultant of a preliminary experiment has shown that the doubling time of cells is about 48 hours. Incidentally, the counting of cell population during the course is carried out by the classical exclusion method using Trypan Blue.

B. Cell Sorting and Endothelial Cell Purification

At the stage when the mixed cells have become confluent and a reasonable number of cells is obtained, endothelial cells are sorted out from among the mixed cells using FACS according to the following protocol. Thus, Dil-acetylated LDL (fluorescent dye marker; product of Biomedical Technologies) (briefly, Dil-Ac-LDL) is added to the mixed cell culture at a concentration of 1 μg/ml, followed by 24-hour incubation. This marker is taken up intracellularly through a scavenger pathway specific to endothelial cells and macrophages. After 24 hours, the cells are trypsinized to prepare a mixed cell suspension and sorting is performed using a cell sorter (FACS machine; product of Bectin Dickenson). According to the size and emission of fluorescence, the cells are sorted into Dil-Ac-LDL-positive cells and cells. After the sorting, these Dil-Ac-LDL-negative types of cells are independently cultured and the culture is continued until $2\times10^6$ endothelial cells are obtained.

C. Tissue Construction

The first step of tissue construction comprises seeding cells in vitro. Specifically, a biodegradable culture matrix is seeded with about $1\times10^6$ cells/cm$^2$ of Dil-Ac-LDL-negative fibroblasts.

Immediately following the seeding of a concentrated cell suspension on the matrix, the system is allowed to stand on the culture dish in a clean bench for 30-60 minutes, and thereafter about 50 ml of a culture medium is added. The culture medium is renewed every day as a rule and after 7 days, that is, one day before surgical transplantation, a further seeding is performed with a suspension of endothelial cells (about $2\times10^6$ cells), whereby a monolayer of endothelial cells is obtained.

The above steps A-C show the cell isolation, culture and seeding procedures for the construction of a heart valve, a pericardium, or a blood vessel.

The following examples are further illustrative of the present invention.

EXAMPLE 1

Construction of a Vascular Regeneration Matrix

A glass test tube (10 mm in outside diameter) was wrapped around with a plain-weave cloth of poly-L-lactide fiber (photograph) in a double-cylindrical form. This assembly was set in a mold (12 mm in inside diameter) and a solution of L-lactide-caprolactone copolymer (50:50) in dioxane (5%) was poured into the clearance, frozen and then lyophilized.

Figure 2:
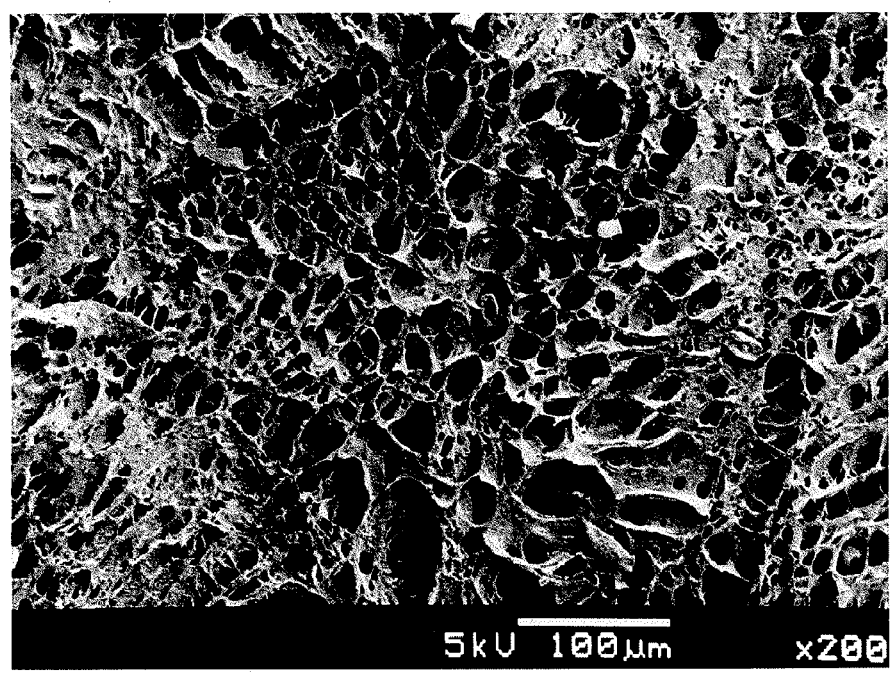
FIG. 2 is a photograph showing a plan view of a vascular regeneration matrix according to the present invention.

The cylindrical vascular prosthesis thus obtained was a cellular substrate reinforced with a fibrous material (FIGS. 1 and 2).

Cell Culture

Through a small skin incision, a peripheral vein segment, about 5 mm long, was excised in a sterile environment and immediately immersed in the tissue culture medium. Cell isolation was carried out by the simple explant technique. As the cell culture medium, the standard cell culture medium DMEM mentioned above was used, and the medium was renewed every 2-3 days. Seeding of Cells The matrix prepared above was seeded with about $1\times10^6$ cells/cm² of a mixed culture of endothelial cells and fibroblasts and the culture was continued for about 1 week until the matrix surface had been completely covered with the cells.

Animal Experiment

Figure 3:
FIG. 3 is a photograph of the angiogram recorded at the $3^{rd}$ postoperative month.

The vascular prosthesis constructed as above was transplanted in the inferior vena cava of a young dog. As a result, no obliteration by rupture was found and a good patency could be verified angiographically at the 3rd postoperative month (the angiograph in FIG. 3) Thoracotomy at 6 months revealed regeneration of the autogenous blood vessel in agreement with the transplantation site.

In contrast, the matrix not reinforced with poly-L-lactide fiber ruptured in one week after substitution and the experimental animal succumbed to sudden death.

What is claimed is:

1. A culture of cardiovascular cells on a matrix to regenerate cardiovascular tissue comprising a sponge made of a bioabsorbable material and a reinforcement,
    the sponge comprising lactic acid (D form, L form, DL form)-caprolactone copolymer,
    the reinforcement comprising at least one member selected from the group consisting of polyglycolic acid and polylactic acid (D form, L form, DL form),
    the reinforcement being integrated with the sponge,
    the reinforcement having a greater strength than the sponge,
    the cardiovascular tissue being at least one member selected from the group consisting of a blood vessel and a cardiac valve, and
    the cardiovascular cells being a mixed cell culture of two or three different kinds selected from the group consisting of endothelial cells, smooth muscle cells and fibroblasts.

2. The culture on the matrix according to claim 1 for use in regenerating an artery, wherein the reinforcement comprises polylactic acid (D form, L form, DL form).

3. The culture on the matrix according to claim 1 for use in regenerating a vein, wherein the reinforcement comprises polyglycolic acid.

4. The culture on the matrix according to claim 1 for use in regenerating a cardiac valve or a pericardium, wherein the reinforcement comprises polylactic acid (D form, L form, DL form).

5. The culture on the matrix according to claim 1, wherein the sponge has a pore diameter of about 5 μm to about 100 μm.

6. A method for regenerating cardiovascular tissue comprising culturing the cells of the culture on the matrix of claim 1.

7. The method for regenerating cardiovascular tissue according to claim 6, wherein the cardiovascular tissue regenerated is a blood vessel.

8. The method for regenerating cardiovascular tissue according to claim 6, wherein the cardiovascular tissue regenerated is a cardiac valve.

9. The culture on the matrix according to claim 1, wherein the reinforcement integrated with the sponge is obtained by lyophilizing a solution comprising lactic acid (D form, L form, DL form)-caprolactone copolymer in contact with a reinforcement selected from the group consisting of a fiber, a nonwoven cloth and a film.

10. The culture on the matrix according to claim 1, wherein the reinforcement has a shape selected from a fiber, nonwoven cloth and film.

* * * * *